United States Patent
Hwang et al.

(10) Patent No.: US 7,628,961 B2
(45) Date of Patent: *Dec. 8, 2009

(54) METHOD AND APPARATUS FOR AMPLIFICATION OF NUCLEIC ACID SEQUENCES BY USING THERMAL CONVECTION

(75) Inventors: Hyun Jin Hwang, Seoul (KR); Jeong Hee Kim, Seoul (KR); Kyunghoon Jeong, Gwangju (KR)

(73) Assignee: Ahram Biosystems, Inc., Seoul (KR)

( * ) Notice: Subject to any disclaimer, the term of this patent is extended or adjusted under 35 U.S.C. 154(b) by 147 days.

This patent is subject to a terminal disclaimer.

(21) Appl. No.: 10/801,342

(22) Filed: Mar. 15, 2004

(65) Prior Publication Data
US 2004/0152122 A1  Aug. 5, 2004

Related U.S. Application Data

(63) Continuation-in-part of application No. PCT/KR02/01728, filed on Sep. 14, 2002.

(30) Foreign Application Priority Data

Sep. 15, 2001  (KR) .................. 10-2001-0057040
Oct. 30, 2001  (KR) .................. 10-2001-0066943

(51) Int. Cl.
*B01J 19/00* (2006.01)
(52) U.S. Cl. ..................... 422/131; 422/138
(58) Field of Classification Search ............. None
See application file for complete search history.

(56) References Cited

U.S. PATENT DOCUMENTS 5,270,183 A    12/1993  Corbett et al.
5,589,136 A    12/1996  Northrup et al.
5,720,923 A *   2/1998  Haff et al. .................. 422/68.1

(Continued)

FOREIGN PATENT DOCUMENTS

EP           0 504 435 A1    9/1992

(Continued)

OTHER PUBLICATIONS

Krishnan, M., et al., "PCR in a Rayleigh-Benard Convection Cell," Science, 298:793, 2002.
Braun, D., et al., "Exponential DNA Replication by Laminar Convection," Physical Review Letters, 91(15):158103-1-158103-4, 2003.

(Continued)

*Primary Examiner*—Kenneth R. Horlick
*Assistant Examiner*—Suchira Pande
(74) *Attorney, Agent, or Firm*—Joseph H. Kim; JHK Law; Robert Buchanan

(57) ABSTRACT

The present invention provides a nucleic acid sequence amplification method and apparatuses thereof that are simple in the design and easy to miniaturize and integrate into complex apparatuses, with capability of using DNA polymerases that are not thermostable. In the present invention, a plurality of heat sources are combined to supply heat to, or remove heat from specific regions of the sample such that a specific spatial temperature distribution is maintained inside the sample by locating a relatively high temperature region lower in height than a relatively low temperature region.

55 Claims, 8 Drawing Sheets

U.S. PATENT DOCUMENTS

| | | | |
|---|---|---|---|
| 5,761,377 A * | 6/1998 | Wolfe et al. | 392/376 |
| 5,919,622 A | 7/1999 | Mancho et al. | |
| 6,168,948 B1 | 1/2001 | Anderson et al. | |
| 6,472,186 B1 * | 10/2002 | Quintanar et al. | 435/91.2 |
| 6,586,233 B2 | 7/2003 | Benett et al. | |
| 6,734,401 B2 * | 5/2004 | Bedingham et al. | 219/388 |
| 2002/0127152 A1 | 9/2002 | Benett et al. | |
| 2005/0074782 A1 | 4/2005 | Krishnan et al. | |

FOREIGN PATENT DOCUMENTS

| | | |
|---|---|---|
| WO | WO 97/48818 A1 | 12/1997 |
| WO | WO 98/25701 A1 | 6/1998 |
| WO | WO0058013 * | 10/2000 |
| WO | WO 02/072267 A1 | 9/2002 |

OTHER PUBLICATIONS

Braun, Dieter, "PCR by Thermal Convection," Modern Physics Letters B, 18(16):775-784, 2004.

Wheeler, E.K., et al., "Convectively Driven Polymerase Chain Reaction Thermal Cycler," Analytical Chemistry, 76(14):4011-4016, 2004.

Hennig, M., and Braun, D., "Conective polymerase chain reaction around micro immersion heater," Applied Physics Letters, 87:183901-1-183901-3, 2005.

Kopp et al., "Chemical Amplification: Continuous-Flow PCR on a Chip," Science 280: 1046-1048 (1998).

* cited by examiner

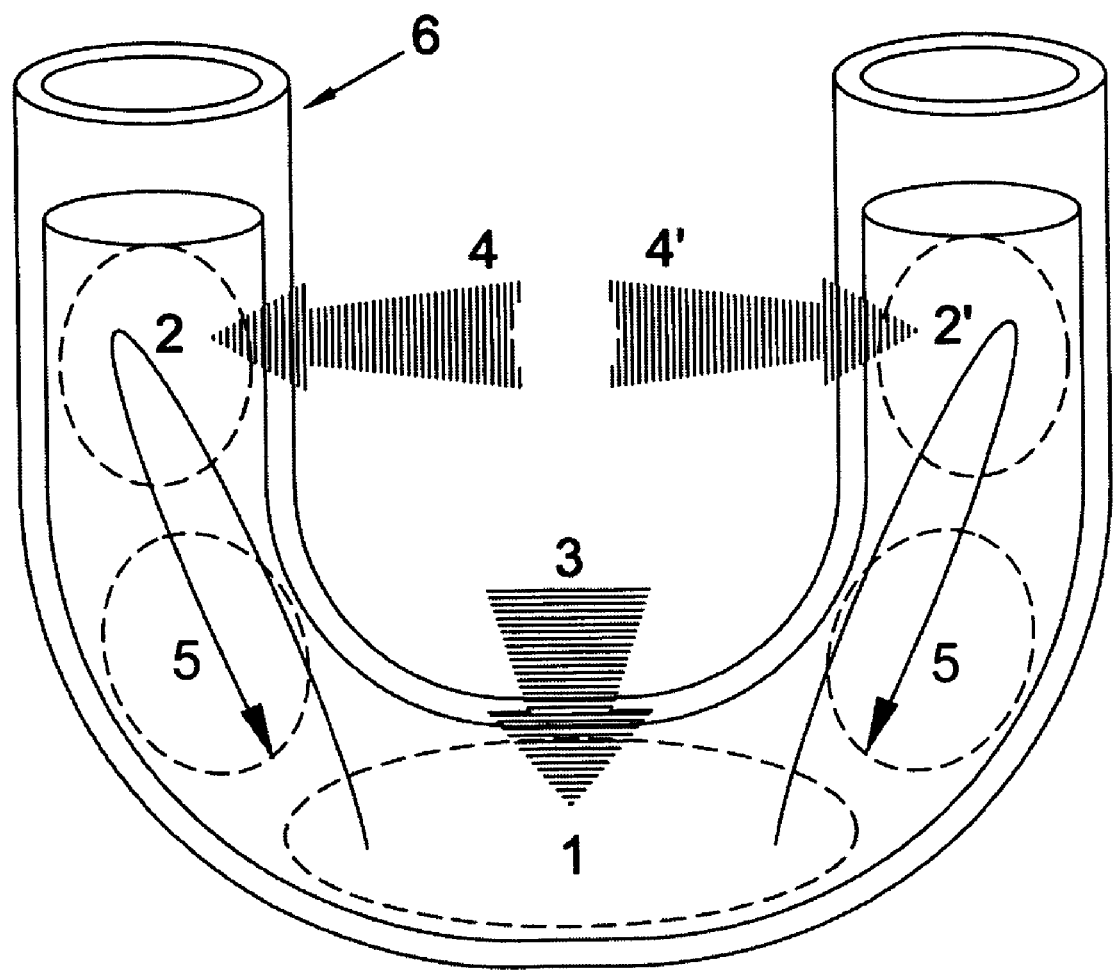

METHOD AND APPARATUS FOR AMPLIFICATION OF NUCLEIC ACID SEQUENCES BY USING THERMAL CONVECTION

CROSS-REFERENCE TO RELATED APPLICATIONS

The present application is a continuation-in-part application claiming benefit of priority to PCT/KR02/01728, filed on Sep. 14, 2002, the contents of which are incorporated by reference herein in its entirety.

TECHNICAL FIELD

The present invention generally relates to methods and apparatuses for amplifying nucleic acid sequences. More particularly, it relates to methods and apparatuses using thermal convection, in which temperature controlled amplification processes including the polymerase chain reaction (PCR) and related processes can be performed to amplify target nucleic acid sequences from genetic samples containing DNA or RNA.

BACKGROUND ART

Nucleic acid sequence amplification technology has a wide application in bioscience, genetic engineering, and medical science for research and development and diagnostic purposes. In particular, the nucleic acid sequence amplification technology using PCR (hereafter referred to as "PCR amplification technology") has been most widely utilized. Details of the PCR amplification technology have been disclosed in U.S. Pat. Nos. 4,683,202; 4,683,195; 4,800,159; and 4,965,188.

Various apparatuses and methods incorporating automated PCR amplification processes have been developed and used for fast and efficient amplification of a variety of genetic samples. The basic working principle of such technology is as follows.

In the commercialized PCR amplification technology, a sample is prepared to contain a template DNA to be amplified, a pair of oligonucleotide primers complementary to a specific sequence of each single strand of the template DNA, a thermostable DNA polymerase, and deoxynucleotide triphosphates (dNTP). A specific portion of the nucleic acid sequence of the template DNA is then amplified by repeating a temperature cycle that sequentially changes the temperature of the sample. Typically, the temperature cycle consists of three or two temperature steps, and the amplification processes during the temperature cycle occur in the following manner.

The first step is the denaturation step in which the sample is heated to a high temperature and double stranded DNAs become separated to single stranded DNAs. The second step is the annealing step in which the sample is cooled to a low temperature and the single stranded DNAs formed in the first step bind to the primers, forming partially double stranded DNA-primer complexes. The last step is the polymerization step in which the sample is maintained at a suitable temperature and the primers in the DNA-primer complexes are extended by the action of the DNA polymerase, generating new single stranded DNAs that are complementary to each of the template DNA strands. The target nucleic acid sequences as selected by the sequences of the two primers are replicated during each cycle consisting of the above three steps. Typically, several millions or higher number of copies of the target nucleic acid sequences can be produced by repeating the temperature cycles for about 20 to 40 times.

The temperature of the denaturation step is typically 90-94° C. The temperature of the annealing step is controlled appropriately according to the melting temperatures ($T_m$) of the primers used, and it typically ranges from 35 to 65° C. It is typical to set the temperature of the polymerization step to 72° C. and use a three-step temperature cycle, since the most frequently used Taq DNA polymerase (a thermostable DNA polymerase extracted from *Thermus aquaticus*) has the optimal activity at that temperature. A two-step temperature cycle in which the polymerization temperature is set to the same as the annealing temperature, can also be used since the Taq DNA polymerase has a broad temperature range of the polymerase activity.

In the most widely used method, a reaction vessel containing the sample is made in contact with a solid metal block having a high thermal conductivity, and the temperature of the solid metal block is changed by combining it with heating and cooling devices to achieve the desired temperature cycling of the sample. The commercial products adopting this type of methods often use a gold-plated silver block that has very high thermal conductivity and/or the Peltier cooling method in order to achieve rapid temperature change. Recently, methods using a fluid such as gas or liquid as a heat source instead of the solid metal block, have been developed to achieve rapid temperature change, and products using such methods are being commercialized. In this type of methods, a fluid heated to a suitable temperature is circulated around the reaction vessel in a manner that an efficient thermal contact can be provided between the fluid heat source and the reaction vessel containing the sample. Other types of methods have also been developed to achieve rapid temperature cycling. Additional examples include a method of contacting the reaction vessel containing the sample or the sample itself sequentially with multiple heat sources each at a specific temperature, a method of heating the sample directly with infrared radiation, etc.

The prior nucleic acid sequence amplification apparatuses have a number of drawbacks as they operate to change the temperature of the whole sample according to the three- or two-step temperature cycle.

Firstly, the prior nucleic acid sequence amplification apparatuses of the temperature cycling type are complex in their design since processes for changing the sample temperature are necessary. In order to perform such temperature change processes, the method incorporating a solid metal block or a fluid as a heat source requires a means for controlling and changing the temperature of the heat source rapidly and uniformly and also a means for controlling the time interval of the temperature change. Similarly, the method of contacting the reaction vessel or the sample sequentially with multiple heat sources each at a specific temperature requires a means for moving the reaction vessel or the sample quickly and precisely and also a means for controlling the moving time and interval.

Secondly, it is difficult to integrate the prior nucleic acid sequence amplification apparatuses in a complex apparatus or a miniaturized device, due to their complicated design. Recently, miniaturized complex apparatuses are under development in the biotechnology field. For example, Lab-on-a-chip has been developed by integrating channels for sample passage, valves, pressure gauges, reaction vessels, detection units, etc. as a single unit on a glass, silicon, or polymer plate using photolithography. Such miniaturized complex apparatuses are expected to have wide applications for various research and medical purposes. In the case that a nucleic acid sequence amplification apparatus needs to be integrated to such miniaturized chip, the prior method has a drawback in miniaturization because it requires a complex design to enable the temperature change processes. Furthermore, it is difficult to integrate the prior apparatuses in a complex apparatus in which rapid temperature change is not desirable.

Thirdly, the prior nucleic acid sequence amplification apparatuses can only use thermostable DNA polymerases such as Taq DNA polymerase. This is because the prior apparatuses have the process of heating the whole sample to a high temperature.

Finally, the prior nucleic acid sequence amplification apparatuses have a limitation for reducing the PCR reaction time. Since the prior apparatuses require the processes for changing the temperature of the whole sample, the PCR reaction time must take more time at least as much as the time needed for the temperature change.

SUMMARY OF THE INVENTION

The present invention is contrived to solve the above problems. It is an objective of the present invention to provide a new nucleic acid sequence amplification method and apparatuses thereof based on thermal convection. The new method and apparatuses according to the present invention achieve amplification of nucleic acid sequences by forming a plurality of specific regions having different temperatures inside the sample and thereby causing natural thermal convection of the sample to occur as a result of the temperature gradient among the different regions.

It is also an objective of the present invention to provide a method and apparatuses thereof that are simpler in their design and do not require complex components such as a means for changing the temperature in a controlled manner and a means for controlling the time interval of the temperature change as are required in the prior temperature cycling methods and apparatuses.

Therefore, it is another objective of the present invention to provide a nucleic acid sequence amplification method and apparatuses thereof that are simpler than the prior art so that they can be readily miniaturized and thus integrated into complex miniaturized apparatuses such as Lab-on-a-chip.

It is still another objective of the present invention to provide a nucleic acid sequence amplification method and apparatuses thereof based on the thermal convection in which not only the thermostable DNA polymerases but also non-thermostable DNA polymerases can be used.

It is still further objective of the present invention to provide a more efficient nucleic acid sequence amplification method and apparatuses thereof that do not require the temperature change processes needed in the prior art.

Other objects and advantages of the invention will become clear to those skilled in the art from the following detailed description, claims, and drawings.

In order to achieve the above objectives, the present invention provides a new nucleic acid sequence amplification method and apparatuses thereof based on the novel thermal convection type operation principle described below.

To achieve the above objectives, the present invention provides a nucleic acid sequence amplification method using PCR, which method comprises:

a step of injecting into a reaction vessel a sample containing a template DNA having target nucleic acid sequences to be amplified, DNA polymerase, deoxyadenosine triphosphate, deoxycytidine triphosphate, deoxyguanosine triphosphate, deoxythymidine triphosphate, and at least two oligonucleotide primers complementary to the 3' terminus of each of the target nucleic acid sequences; and a step of maintaining a specific spatial temperature distribution in the sample by contacting thermally with the sample a plurality of heat sources which supply heat to, or remove heat from specific regions of the sample such that a relatively high temperature region is located lower in height than a relatively low temperature region, wherein the specific spatial temperature distribution comprises specific spatial regions each fulfilling a temperature condition suitable for (i) a denaturation step in which double stranded DNAs become separated to single stranded DNAs, (ii) an annealing step in which the single stranded DNAs formed in the denaturation step hybridize to the primers to form DNA-primer complexes, or (iii) a polymerization step in which the primers in the DNA-primer complexes are extended by the polymerization reaction, and wherein the specific spatial temperature distribution is a temperature distribution that induces circulation of the sample by thermal convection so that the denaturation, annealing, and polymerization steps occur sequentially and repeatedly inside the sample.

To achieve the above objectives, the present invention provides a nucleic acid sequence amplification apparatus using PCR, which apparatus comprises:

a plurality of heat sources which may supply heat to, or remove heat from a plurality of specific regions in a sample contained in a reaction vessel, wherein the heat sources are arranged to maintain a specific spatial temperature distribution in the sample such that a relatively high temperature region is located lower in height than a relatively low temperature region, wherein the specific spatial temperature distribution comprises specific spatial regions each fulfilling a temperature condition suitable for (i) a denaturation step in which double strand DNAs become separated to single strand DNAs, (ii) an annealing step in which the single strand DNAs formed in the denaturation step hybridize to the primers to form DNA-primer complexes, or (iii) a polymerization step in which the primers in the DNA-primer complexes are extended by the polymerization reaction, and wherein the specific spatial temperature distribution is a temperature distribution that induces circulation of the sample by thermal convection so that the denaturation, annealing, and polymerization steps occur sequentially and repeatedly inside the sample.

In the present invention, spatial regions are generated inside the reaction vessel containing the sample, in which regions the denaturation, annealing, and polymerization steps can occur sequentially and repeatedly. In order to achieve this, a plurality of heat sources are combined to supply heat to, or remove heat from the specific regions of the sample, and moreover a relatively high temperature region is located to be lower in height than a relatively low temperature region. This results in generation of a natural thermal convection as a result of the temperature gradient between the specific regions, thereby causing circulation of the sample among the different temperature regions. Thus, the denaturation, annealing, and polymerization steps can occur sequentially and repeatedly, resulting in amplification of nucleic acid sequences.

As described, the nucleic acid sequence amplification apparatuses of the present invention are based on the thermal convection method and it has the following characteristics in their design. Firstly, the apparatus of the present invention requires a plurality of heat sources that can maintain a plurality of specific temperature regions in the sample inside the reaction vessel at selected temperatures. Secondly, a relatively high temperature region should be positioned lower in height than a relatively low temperature region so as to induce circulation of the sample among the specific temperature regions via thermal convection. More specifically, the sample in the high temperature region has a lower density than that in the low temperature region. Therefore, the buoyant force is generated and it causes the sample to move from the high temperature region at the lower position to the low temperature region at the higher position, while the gravitational force causes the sample to move in the opposite direction. A natural thermal convection is thus generated by the temperature difference, resulting in circulation of the sample among the specific temperature regions. Finally, the temperatures of the specific temperature regions should be selected such that spatial regions, in which the denaturation, annealing, and polymerization steps can occur in each region, can be formed in the sample and also the three steps can be performed sequentially and repeatedly by thermal convection-induced circulation of the sample among the specific temperature regions at an appropriate speed.

The objectives, features and advantages described above will be apparent from the following detailed description provided in connection with the attached drawings. In describing the present invention, detailed explanation on the related prior art will be omitted when it can unnecessarily make the points of the present invention ambiguous.

BRIEF DESCRIPTION OF DRAWINGS

FIGS. 2a and 2b show schematic diagrams of the cases having more than three specific temperature regions in the sample.

Figure 1:
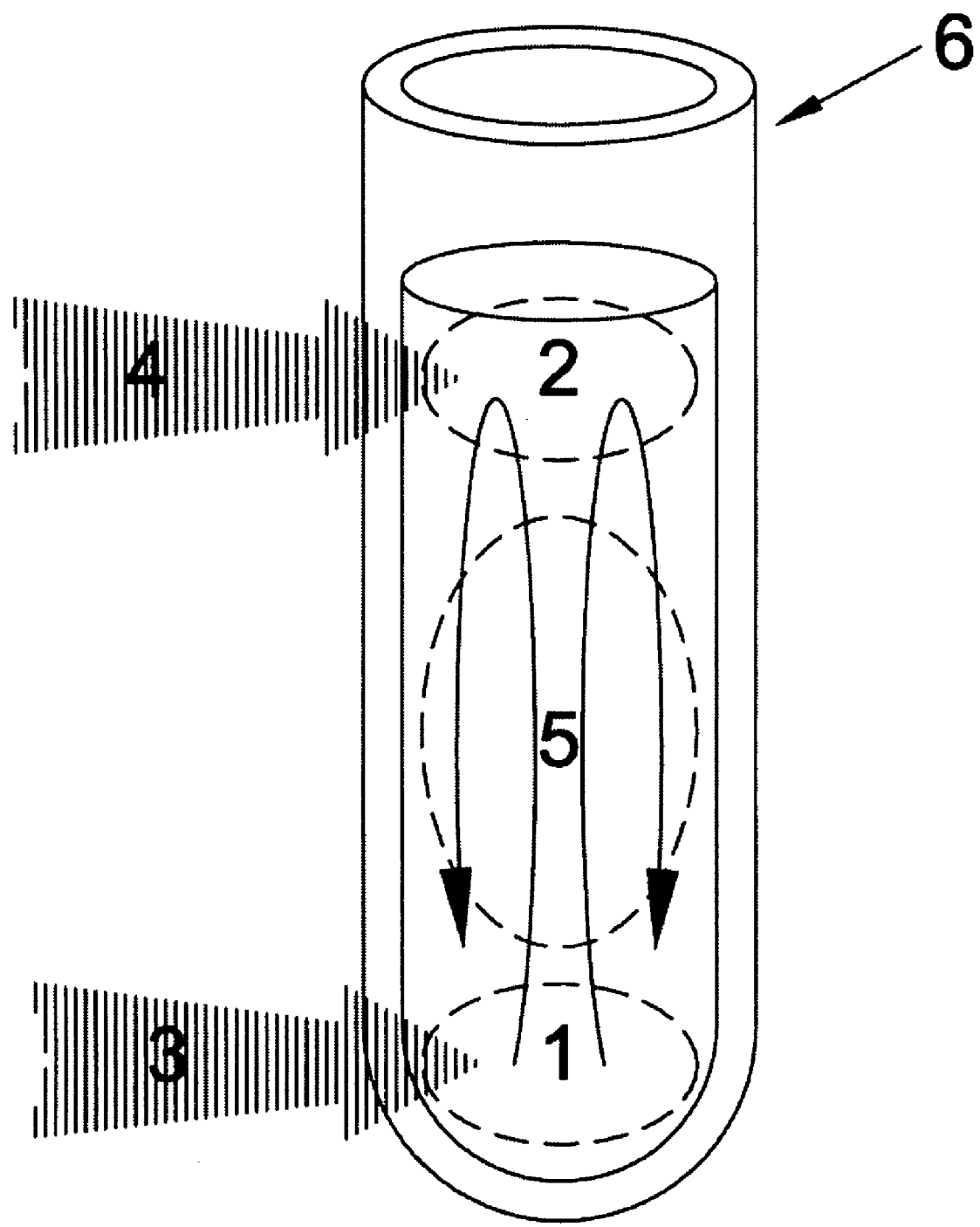
FIG. 1 shows a schematic diagram of the operation principle of the nucleic acid sequence amplification method based on the thermal convection.

Explanation on the numbers of the important parts in the drawings 1, 1': High temperature region
2, 2': Low temperature region
3, 4, 3', 4': Heat source
5: Convection region
6: Reaction vessel
101: First conduction block
102: Second conduction block
103: Reaction vessel
104: Heating device
105: Inlet of temperature control fluid
106: Outlet of temperature control fluid
107: Insulator
112, 117: Through hole
111: Opening

DETAILED DESCRIPTION OF THE INVENTION

As used herein, by "height" it is generally meant vertical height.

As used herein, "reaction vessel" refers to any container, which may contain a sample comprising nucleic acid in which a PCR reaction may occur by thermal convection. The reaction vessel may be made of a wide variety of material so long as it is capable of conducting heat and is able to impart heat to or remove heat from the sample. The reaction vessel is not limited by size or shape so long as a PCR reaction is capable of being carried out through thermal convection. For example, although FIG. 3 exemplifies what looks to be a straight cylindrical reaction vessel, the invention is not bound by any particular shape. For instance, the reaction vessel may be tapered from top to bottom or from bottom to top, so long as thermal convection is capable of being established within the sample in the reaction vessel.

As used herein, the "first conduction block" refers to the heat conductive element that generally imparts heat to the sample.

As used herein, the "second conduction block" refers to the heat conductive element that generally removes heat from the sample. In this regard, the apparatus depicted in FIG. 3 is for illustration only and various modifications and improvements are possible, so long as that the second conduction block is capable of removing heat from the sample at the site of contact. In one embodiment, the apparatus depicted in FIG. 3 may be modified to improve the thermal contact of the heat source with the sample. For instance, the second thermally conductive block 102 that works as a cooling unit may be modified so as to make physical contact with the sample itself instead of being in contact with the reaction vessel. In another embodiment, the shape of the second thermally conductive block may be modified to comprise a plurality of protrusions in the shape of dip sticks each of which may fit into the opening of the reaction vessel on the top and thus make physical contact with the upper portion of the sample.

In yet another embodiment, the second thermally conductive block may be modified to comprise a plurality of receptors that fit to a plurality of dip sticks. In this embodiment, each of the dip sticks may be installed in the opening on the top of the reaction vessel and make physical contact with the upper portion of the sample and also with one of the receptors included in the second thermally conductive block.

BEST MODE FOR CARRYING OUT THE INVENTION

Below, the preferred embodiments according to the present invention are explained in detail referring to the attached drawings.

FIG. 1 shows a schematic diagram of the operation principle of the nucleic acid amplification method based on the thermal convection. The embodiment shown in FIG. 1 exemplifies the case in which a straight tubing with its one end closed is used as a reaction vessel and two specific temperature regions 1 and 2 are generated. However, as shown in the embodiments depicted in FIG. 2, reaction vessels having modified shapes may be used and three or more specific temperature regions may be generated. It should be apparent to those skilled in the art that various modifications including those described above may be contemplated based on the thermal-convection operation principle of the nucleic acid amplification method according to the present invention.

In one embodiment as shown in FIG. 1, the reaction vessel is in thermal contact with two heat sources 3 and 4 that supplies heat to, or removes heat from the specific regions 1 and 2 in the sample directly or indirectly through the wall of the reaction vessel, thereby forming a spatial temperature distribution in the sample. The temperature distribution thus formed allows the three steps, the denaturation, annealing, and polymerization steps required in PCR to occur. Among the two regions 1 and 2 having different temperatures, the relatively high temperature region 1 is positioned lower in height than the relatively low temperature region 2. The temperature difference generates density difference in the sample. The buoyant force exerted on the low density sample in the high temperature region 1 and the gravitational force exerted on the high density sample in the low temperature region 2 generate a thermal convection of the sample. Thus the sample naturally circulates among the different spatial regions in each of which the denaturation, annealing, and polymerization steps can occur. This design makes the three PCR steps occur sequentially and repeatedly, thereby achieving amplification of DNA nucleic acid sequences by the PCR process. A more detailed operation is exemplified below.

For instance, the high temperature region 1 located at a lower portion of the sample may be maintained at a temperature between 90 to 94° C. at which temperature double strand DNAs can be separated into single strand DNAs. Such arrangement makes the denaturation step occur mainly in the region 1. The low temperature region 2 located at an upper portion of the sample may be maintained at the annealing temperature between 35 to 65° C. so that the DNAs denatured at the high temperature region at the lower portion moves to the low temperature region at the upper portion by thermal convection, and therefore the single stranded DNAs can anneal with the primers that are complementary to the single stranded DNAs, forming DNA-primer complexes. In this arrangement, if Taq DNA polymerase, known to have its optimal activity at 72° C. and a wide temperature range of activity even to low temperature, is used for polymerization, the polymerization step, where DNA polymerase binds to the DNA-primer complex and the primer is extended, can occur in the low temperature region 2 and at the upper portion of the convection region 5. Therefore, the denaturation step occurs first in the high temperature region 1 and the denatured DNAs move to the low temperature region 2 by thermal convection. The annealing step thus occurs in the low temperature region in the presence of the primers. The polymerization step finally occurs in the presence of DNA polymerase during the time period that the DNA-primer complexes formed in the annealing step are passing through the low temperature region 2 and the convection region 5 by thermal convection. Consequently, the denaturation, annealing, and polymerization steps can occur sequentially and repeated, thereby amplifying efficiently the target sequences of the sample DNA.

Figure 2A:
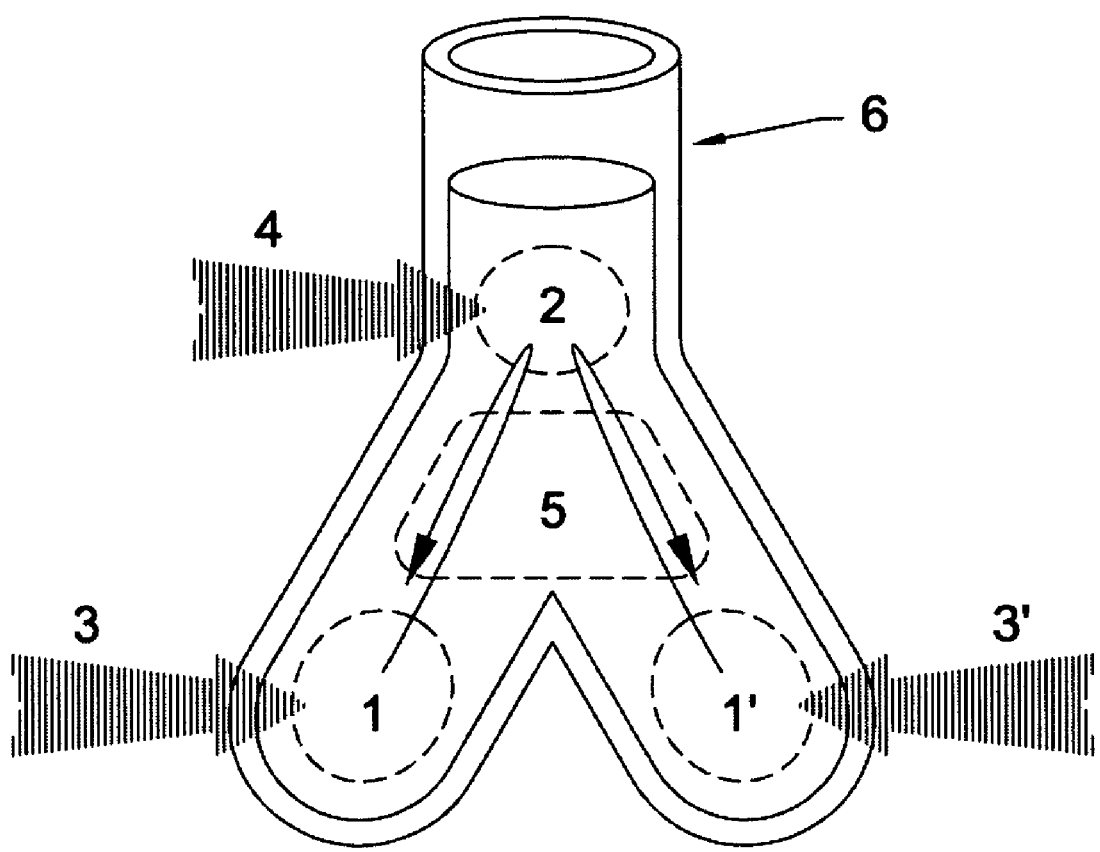

In other embodiments as shown in FIG. 2, it is contemplated that three specific regions of the reaction vessel are in thermal contact with a plurality of heat sources. FIG. 2a shows a schematic diagram illustrating one embodiment in which a plurality of heat sources 3, 3', and 4 are arranged to form two high temperature regions 1 and 1' and one low temperature region 2. FIG. 2b shows a schematic diagram illustrating another embodiment in which a plurality of heat sources 3, 4, and 4' are arranged to form one high temperature region 1 and two low temperature regions 2 and 2'. The plurality of the heat sources used herein may be arranged separately for each temperature region or a same heat source may be used for more than one temperature regions. In the embodiment illustrated in FIG. 2a, if the two high temperature regions 1 and 1' are designed for the denaturation and polymerization steps, respectively, each region should be contacted with a heat source that can maintain the temperature of that region suitable for each step. In the embodiment illustrated in FIG. 2b, if both of the two low temperature regions 2 and 2' are designed for the annealing step, it is preferable to use one heat source in replacement of the two heat sources 4 and 4'. In addition, FIG. 2b shows that it is possible according to the present invention to construct a reaction vessel having separate sample inlet and outlet.

In order to improve the efficiency of the present invention, it is important to control the speed of the thermal convection such that the reaction at each step can occur sufficiently and at the same time the total reaction time can be reduced. This can be achieved by (a) controlling the temperature gradient between the specific temperature regions, (b) controlling the diameter of the reaction vessel, or (c) changing the material of the reaction vessel. When controlling the temperature gradient to adjust the thermal convection speed, it is most convenient to vary the temperature difference between the specific temperature regions. However, this has a limitation since each of the specific temperature regions has its own function for PCR that is dependent on temperature. Therefore, the distance between the high temperature region (1 and 1') and the low temperature region (2 and 2') may be varied to obtain the same effect. For instance, the temperature gradient becomes smaller as the distance between the two temperature regions becomes larger if the temperature difference remains the same, and thus the thermal convection speed becomes reduced. Since the adhesion force between the wall of the reaction vessel and the sample is a factor that inhibits the thermal convection, the thermal convection speed can be controlled by adjusting the diameter of the reaction vessel. As the ratio of the surface area of the reaction vessel in contact with the sample relative to the volume of the sample becomes larger, the adhesion force increases and the thermal convection speed decreases. Therefore, the thermal convection speed can be controlled by adjusting the diameter of the reaction vessel, thereby controlling the surface area of the reaction vessel in contact with the sample. The adhesion force between the sample and the wall of the reaction vessel also has an intimate relation with the material of the reaction vessel. Because the PCR process is normally performed in an aqueous solution, hydrophobic materials such as polyethylene and polypropylene that have weaker adhesion force with water give rise to higher convection speeds as compared to hydrophilic materials such as glass. Therefore, the efficiency of the present invention can be improved further by designing the reaction vessel suitable for the PCR reaction kinetics based on the principles described above.

Figure 3A:
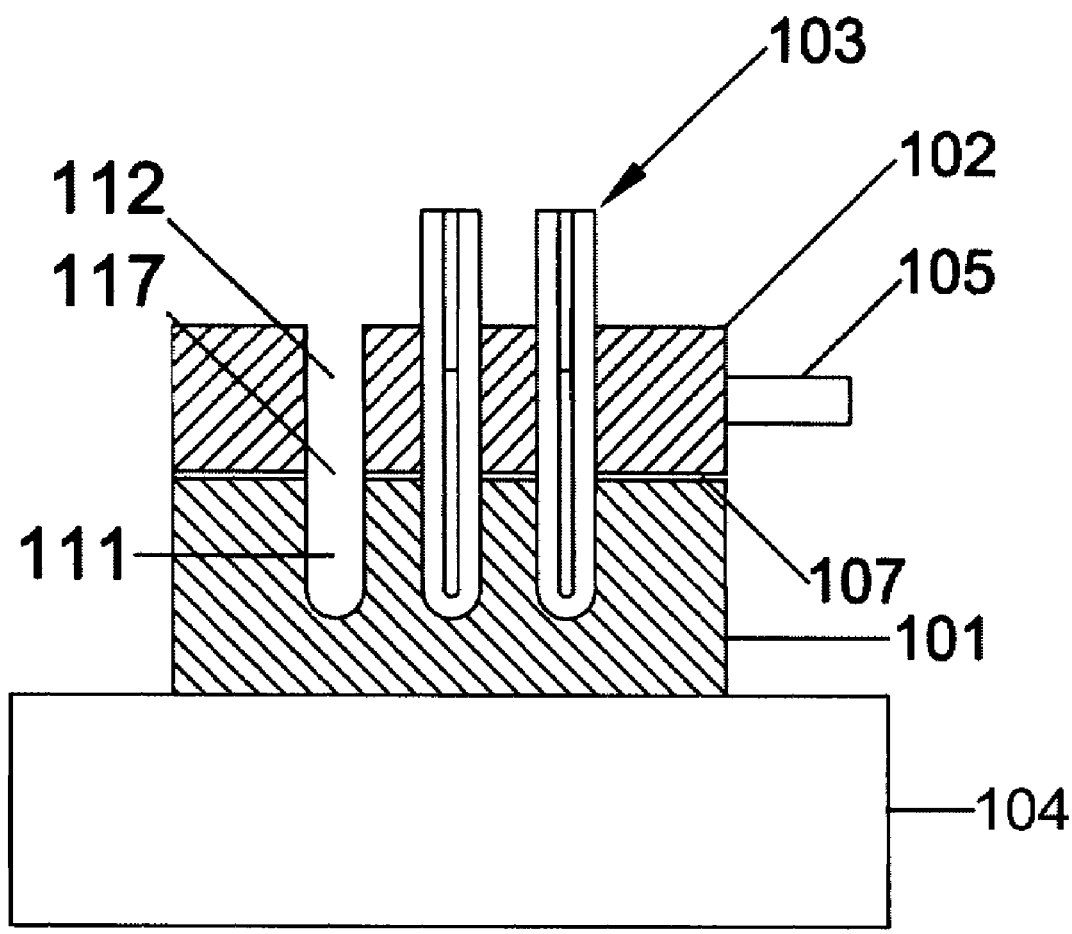
FIGS. 3a and 3b show a cross sectional view and a perspective view, respectively, of the nucleic acid sequence amplification apparatus according to the present invention.
Figure 3B:
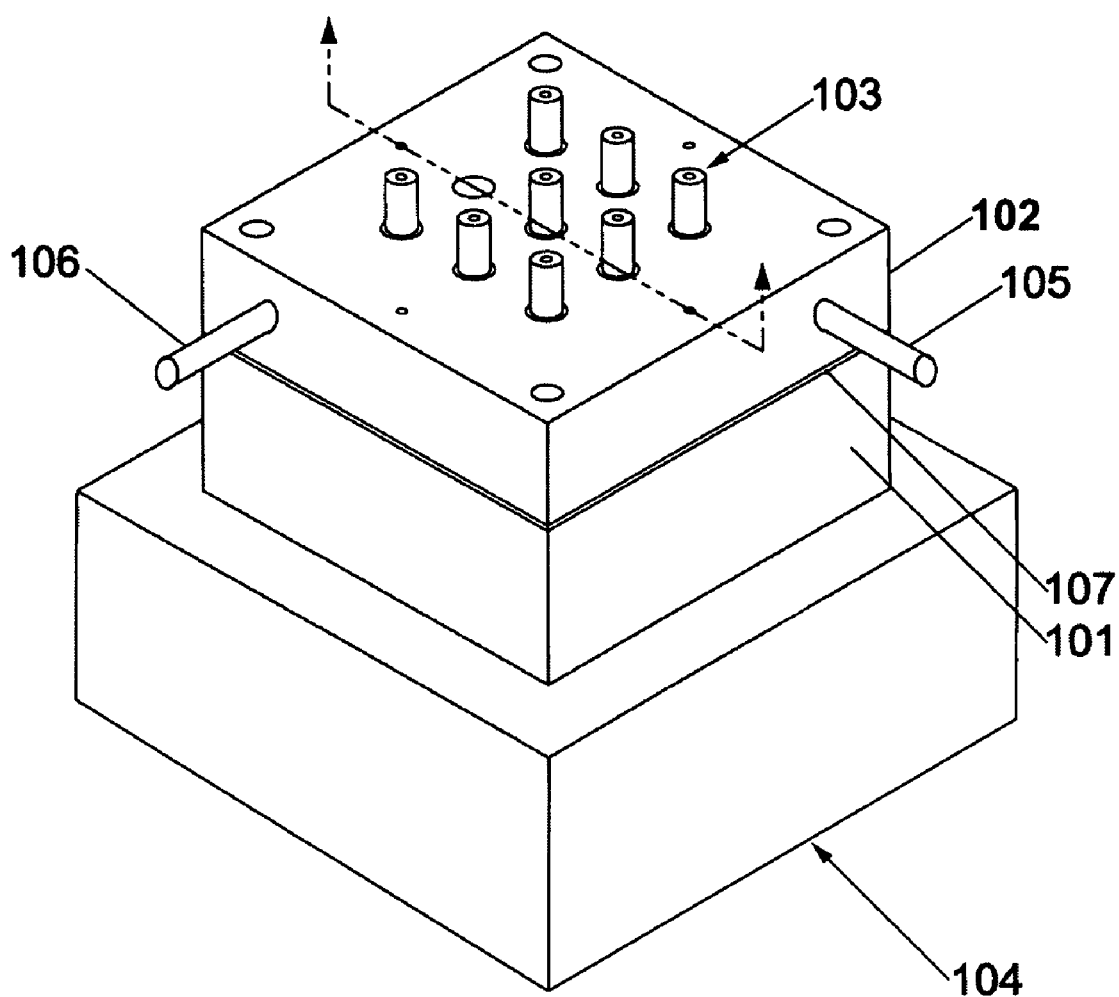

FIG. 3 shows a cross sectional view (FIG. 3a) and a perspective view (FIG. 3b) of the nucleic acid sequence amplification apparatus according to one embodiment of the present invention. The apparatus shown in FIG. 3 comprises a plurality of heat sources as means for maintaining temperature, which include a heating unit; a cooling unit; or a combination of a heating unit and a cooling unit. Preferably, an insulating means may be included in between the heat sources to thermally insulate the heat sources. In this particular embodiment, the apparatus comprises first and second heat sources that are in thermal contact with specific regions of the sample. The first heat source consists of a first thermally conductive block 101 and an electric heating unit 104 that supplies heat to the first thermally conductive block. The first thermally conductive block is in thermal contact with a lower portion of the reaction vessel to form a high temperature region at a lower portion of the sample. The second heat source consists of a second thermally conductive block 102 and a circulating water bath that circulates water at certain temperature through the inside of the second thermally conductive block to maintain the temperature of the second thermally conductive block at a suitable temperature. The second thermally conductive block 102 is in thermal contact with an upper portion of the reaction vessel to form a low temperature region at an upper portion of the sample. The second thermally conductive block 102 comprises an inlet 105 though which water flows in from the water bath, an outlet 106 through which the water flows out, and a fluid circulation channel for circulating the water inside the second thermally conductive block. Although the fluid circulation channel in the second thermally conductive block is not depicted in FIG. 3, the person skilled in the art can understand that the fluid circulation channel is designed to transfer heat uniformly to the second thermally conductive block 102. The material of the thermally conductive blocks 101 and 102 is selected to be copper that has a high thermal conductivity, and an insulator 107 is inserted between the two blocks to prohibit direct heat transfer. The first and second thermally conductive blocks 101 and 102 have receptor openings for introduction of the reaction vessels. The receptor opening consists of an opening 111 having its one end closed in the first thermally conductive block 101, a through hole 112 in the second thermally conductive block, and another through hole 117 in the insulator.

In Example 1, 2, and 3 described later, the high temperature region at a lower portion of the sample is maintained at 94° C. by controlling the electric heating unit 104, and the low temperature region at an upper portion of the sample at 45° C. by controlling the temperature of water in the circulating water bath.

The present invention is not limited to the nucleic acid sequence amplification apparatus depicted in FIG. 3. The following modifications are possible.

Firstly, the structures of the thermally conductive blocks 101 and 102 may be modified. For instance, the first thermally conductive block 101 may be contacted thermally with a lower portion of the reaction vessel and the second thermally conductive block 102 with an upper portion of the reaction vessel, while an intermediate portion of the reaction vessel may be contacted with air or a third thermally conductive block. In addition, different from the embodiment depicted in FIG. 3 in which heat is transferred from the blocks to the specific regions of the sample through the wall of the reaction vessel, the thermally conductive blocks may be contacted directly with the sample.

Secondly, the material of the thermally conductive blocks may be modified. In the embodiment depicted in FIG. 3, the thermally conductive blocks 101 and 102 made of copper are used, but the material is not limited to copper. Nearly any material that can transfer heat to the reaction vessel may be used. For instance, other thermally conductive solid or fluid such as liquid or gas may be used in replacement of the thermally conductive blocks used above. For some instance, infrared radiation or other means may be used in replacement of some or all of the thermally conductive blocks 101 and 102.

Thirdly, means for maintaining the temperatures of the first and second thermally conductive blocks are not limited to a circulating water bath or an electric heating unit. Nearly any unit that can supply heat to, remove heat from the sample may be used.

Fourthly, nearly any means such as solid, liquid, or gas may be used in replacement of the insulator 107 depicted in FIG. 3 as far as it is suitable for insulating heat transfer between conductive materials. It is also possible to use a composition that does not include the insulator.

Finally, when a modified reaction vessel (for example, those shown in FIG. 2a or 2b) is used instead of the reaction vessel illustrated in FIG. 1 to facilitate the thermal convection, one may use a plurality of heat sources including thermally conductive blocks and their modifications that are suitably modified based on the principle of the present invention The first, second, and third cases described above are examples in which a part of the heat source, particularly the thermally conductive block, is modified. As used herein, the heat source refers to any means that can be used for maintaining the temperature of the sample at a specific value. Therefore, in addition to the modification examples of the heat sources described above, any device may be used as a heat source in the present invention as far as it can be used to maintain a specific region of the sample at a selected temperature. The present invention includes nearly any apparatus that has a function of maintaining specific regions of the sample at selected temperatures. This is because the present invention is characterized not by a particular design of the heat sources but by the special arrangement of the heat sources intended for generating a specific temperature distribution inside the sample that enables the PCR process to occur sequentially and repeatedly.

More detailed designs of the modification examples described above may be varied depending on the development of industrial technologies. Therefore, detailed explanations are omitted.

Figure 4:
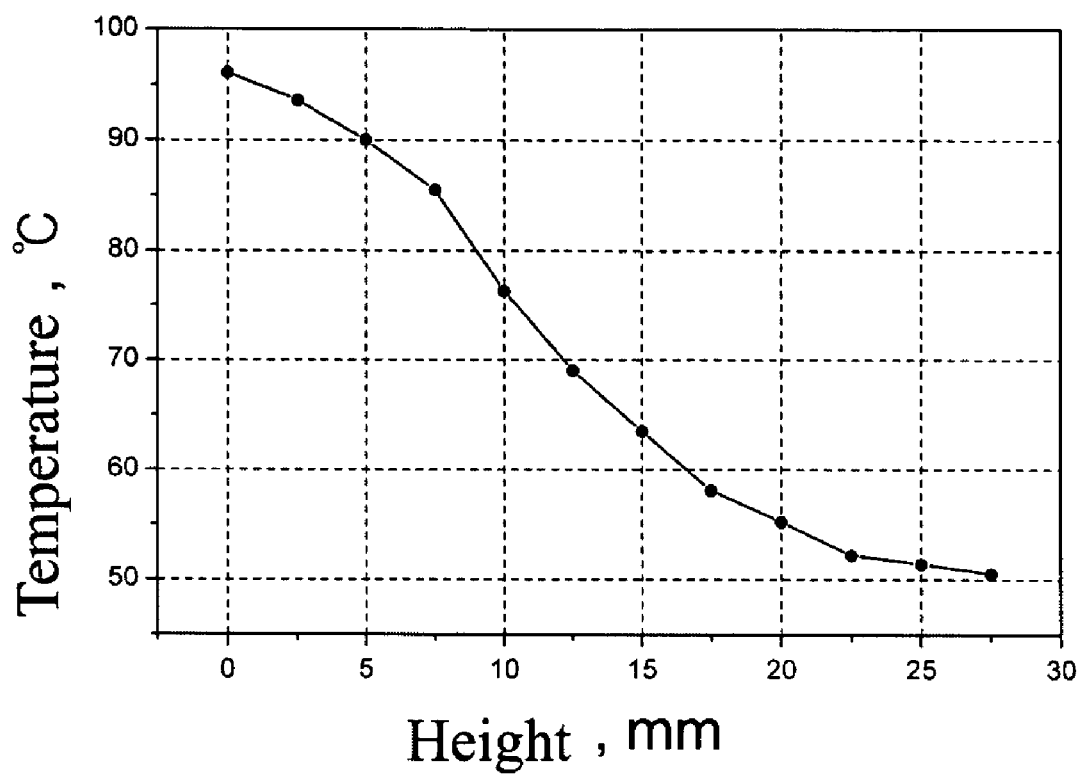
FIG. 4 shows the temperature distribution of the sample at various heights in the reaction vessel.

FIG. 4 shows a temperature distribution measured at various heights from the bottom of the reaction vessel, demonstrating the principle of the PCR process based on the thermal convection. The thermal convection is a phenomenon by which movement of fluid is induced by a density difference generated by difference in temperature. This type of convection is referred to as a natural convection, distinguished from a forced convection where fluid is forced to move by a pump or a propeller. The term convection as used in the present invention always refers to a natural convection. For a natural convection to occur in the reaction vessel, a lower portion of the sample in the reaction vessel should be higher in temperature than an upper portion.

As can be seen in FIG. 4, when the first thermally conductive block 101 contacting with a lower portion of the reaction vessel is maintained at 96° C. and the second thermally conductive block 102 contacting with an upper portion at 45° C., the high temperature region (the region with the temperature higher than or equal to 90° C. in FIG. 4), the low temperature region (the region with the temperature near 50° C.), and the convection region (the region having a temperature gradient) are formed. The sample is subject to the denaturation step in the high temperature region. The denatured sample then moves to the low temperature region across the convection region, in which the sample is subject to the annealing step. While staying in the low temperature region and moving back through the convection region from the low temperature region, the sample is subject to the polymerization step. Thermal convection causes the sample to circulate the three regions sequentially and repeatedly, thereby leading to amplification of nucleic acid sequences by PCR.

Figure 7:
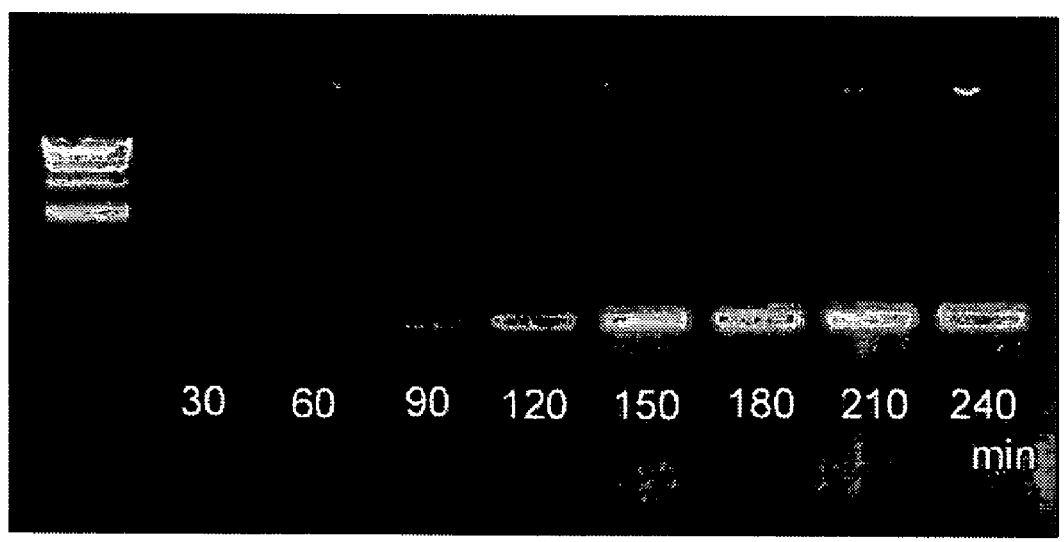
FIG. 7 is a photograph of the electrophoresis result illustrating results of Example 3 at various reaction times.

FIG. 7 shows the results obtained by using DNA polymerase immobilized on the solid surface. The term "immobilized DNA polymerase" as used herein is meant a DNA polymerase that is immobilized on a solid support with its polymerase activity preserved. Various methods may be used to prepare the immobilized DNA polymerase, but it should provide an immobilized DNA polymerase that has a high enough polymerase activity so as to enable detection of nucleic acid sequences amplified by PCR of template DNAs. The immobilized DNA polymerase used in the examples of the present invention was prepared to preserve a high polymerase activity by using a method in which the active site of the DNA polymerase was masked by a DNA substrate and immobilized on a Au surface by covalent bonding. Detailed procedure of the immobilization method is described in the example. The polymerase activity of the immobilized enzyme as prepared by this method was high enough (about 60-80% compared to the solution phase DNA polymerase) to use for PCR. However, the immobilized DNA polymerase that can be used with the present invention is not limited to those prepared by the method used in the example of the present invention, but includes those prepared by other methods.

In the nucleic acid sequence amplification method of the thermal convection type according to the present invention, DNA polymerases that are not thermostable, such as Klenow fragment and T7 DNA polymerase, may be used in addition to the thermostable polymerases such as Taq DNA polymerase. This is due to the following fact. By the virtue of the characteristics of the present invention, the temperature of the total sample does not change from a high temperature to a low temperature or vice versa repeatedly, but the specific regions in the sample are maintained at constant temperatures. For instance, an upper portion of the sample may be maintained at a low temperature, whereas a lower portion of the sample may be maintained at a high temperature. It is possible to use DNA polymerase that is not thermostable, by locating the immobilized DNA polymerase in the low temperature region or in the upper portion of the convection region near the low temperature region.

EXAMPLES

Example 1, 2, and 3 described below confirm that the objectives of the present invention can be achieved using a nucleic acid sequence amplification apparatus of the present invention.

Example 1

1. Methods
1.1. Reaction vessel

A glass tubing with its one end closed was used as a reaction vessel. The glass tubing had a length of 55~60 mm, an inner diameter of 2 mm, an outer diameter of 8 mm, and a thickness of 3 mm at the bottom-side closed end. The inner wall of the glass tubing was coated with polytetrafluoroethylene using a spray type coating material and thermally hardened.

1.2. Sample pBluescript II KS(+) was used as a template DNA. The sample used in PCR contained 40 ng of the template DNA, 40 pmol each of T3 primer (5'-ATTAACCCTCACTAAAG-3') (SEQ ID NO: 1) and T7 primer (5'-AATACGACTCAC-TATAG-3') (SEQ ID NO: 2), 4 nmol of dNTP, 1 pmol (5 U) of Taq DNA polymerase, and 250 nmol of $MgCl_2$ in 100 μl of 10 mM Tris buffer at pH 8.3 containing 50 mM KCl.

1.3. Reaction Temperature and Reaction Time

Firstly, the first thermally conductive block 101 was heated with an electric heating unit and maintained at 96° C., and the second thermally conductive block 102 was maintained at 45° C. using a circulating water bath. The sample prepared above was injected to the reaction vessel, and the reaction vessel was then inserted into the receptor 111, 117, and 112. The sample was allowed to react for a suitable time. During the reaction, the reaction vessel was pressurized to about 1.2 atm by adding nitrogen gas to prevent boiling of the sample solution.

1.4. Measurement of the Temperature Distribution in the Sample

The temperature in each region of the sample was measured under the above reaction conditions. The tip of a thermocouple thermometer was placed every 2.5 mm from the bottom of the reaction vessel, and the temperature was measured and recorded after sufficient time. An example of the temperature distribution of the sample in the reaction vessel is shown in FIG. 4.

2. Results

First, the measured temperature in each region of the sample in the reaction vessel under the above reaction conditions confirmed (see FIG. 4) that a high temperature region above 90° C. for denaturation, a low temperature region around 50° C. for annealing, and a convection region having a temperature gradient for induction of the thermal convection are formed. Polymerization is expected to occur in the low temperature region and the upper portion of the convection region.

Figure 5:
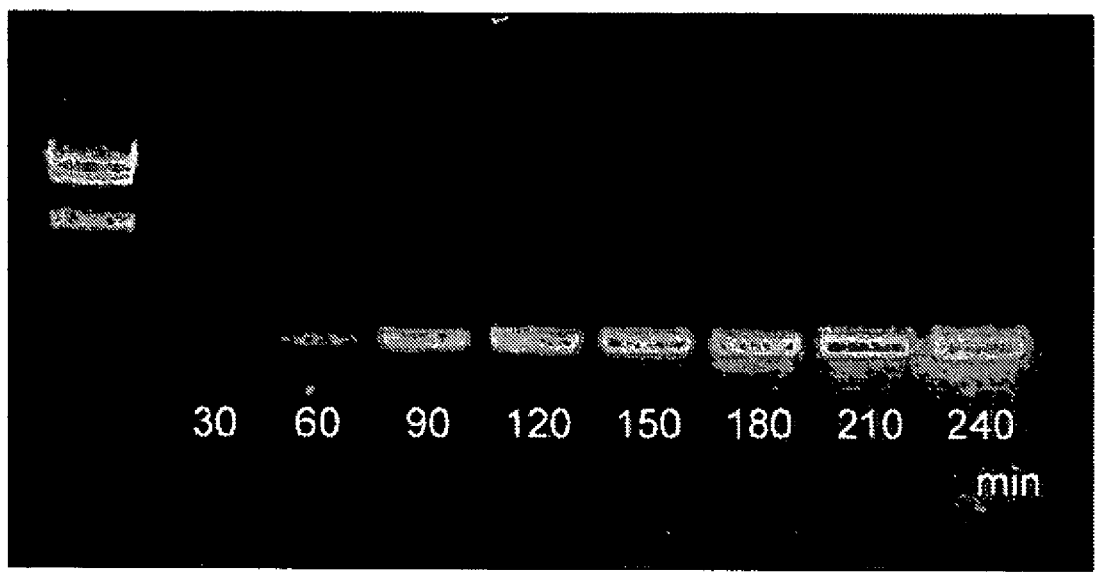
FIG. 5 is a photograph of the electrophoresis result illustrating results of Example 1 at various reaction times.

After the sample was incubated for a given reaction time under the above reaction conditions, the reaction vessel was taken out and cooled. The reaction products were analyzed by electrophoresis using 1.0% agarose gel. FIG. 5 is a photograph of the electrophoresis results obtained at the reaction times up to 4 hours for every 30 min time interval. The reaction product is a 164 bp double stranded DNA. As can be seen in FIG. 5, the PCR reaction reaches saturation before 90 min.

Example 2

1. Methods

In addition to T3/T7 primer pair, KS/U, KS/Pvu ||, and KS/Nae I primer pairs were also examined in the experiments. The reaction time was set to 150 min, and other reaction conditions were the same as in Example 1. The sequences of the T3 and T7 primers were described in Example 1, and the sequences of other primers are given as follows:

```
KS primer:
5'-CGAGGTCGACGGTATCG-3'           (SEQ ID NO: 3)

U primer:
5'-GTAAAACGACGGCCAGT-3'           (SEQ ID NO: 4)

Pvu || primer:
5'-TGGCGAAAGGGGGATGT-3'           (SEQ ID NO: 5)

Nae I primer:
5'-GGCGAACGTGGCGAGAA-3'           (SEQ ID NO: 6)
```

2. Results

Figure 6:
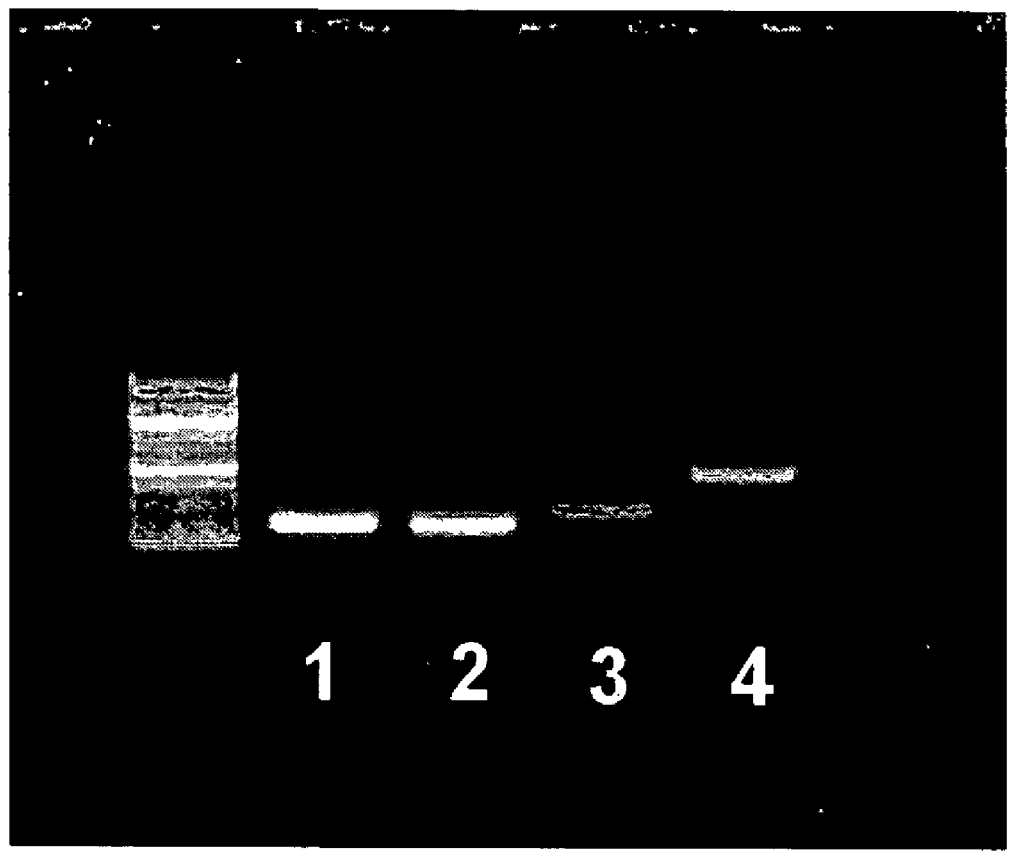
FIG. 6 is a photograph of the electrophoresis result illustrating results of Example 2 for each pair of primers.

As in Example 1, the reaction products were analyzed by electrophoresis. FIG. 6 is a photograph of the electrophoresis results of Example 2, where lanes 1, 2, 3, and 4 are the results obtained with T3/T7, KS/U, KS/Pvu ||, and KS/Nae I primer pairs, respectively. It can be seen that the four primer pairs produced double stranded DNAs with correct sizes of 164 bp, 144 bp, 213 bp, and 413 bp, respectively.

Example 3

1. Methods

Instead of adding Taq DNA polymerase to the sample, Taq DNA polymerase was immobilized on the surface of a Au wire and it was located in the low temperature region. Other experimental conditions were the same as in Example 1.

The method used to immobilize the DNA polymerase is described below.

The 65 base single stranded DNA and the KS primer shown below were mixed in a pH 8.3 phosphate buffer at 1:1 molar ratio. The resulting solution was incubated at 94° C. for 10 min and then cooled down slowly below 35° C. During this process, the 65 base single stranded DNA and the KS primer were annealed to form a partially double stranded DNA. An appropriate number of moles of Taq DNA polymerase (AmpliTaq Gold) purchased from Perkin Elmer (U.S.A.) was then added to this solution and the resulting mixture was incubated in a dry bath at 72° C. for 10 min. Then, the mixture was moved to a dry bath at 50° C. and incubated for 20 min to finish preparation of a masked DNA polymerase in which the partially double stranded DNA is bound to the active site of the DNA polymerase.

```
KS primer:
5'-CGAGGTCGACGGTATCG-3'                                          (SEQ ID NO: 1)

65-mer:
3'-CCAGCTGCCATAGCTATTTTCTTTTCTTTCTTAAGTTCTTTTCTTTTCCTAGG         (SEQ ID NO: 7)

TGATCAAGATCT-5'
```

In order to have a maximum amount of immobilized DNA polymerase be 0.26 pmol, Au wire having an outer diameter of 0.1 mm and a length of 4.7 cm was prepared and used after manipulating it to a coil shape having an outer diameter of 1.5 mm and a length of about 4 mm. In order to ensure the cleanness of the surface of the Au wire, it was washed with Piranha solution for 10~15 minutes at 60~70° C. and was rinsed with deionized water and subsequently with absolute ethanol, right before using.

In order to introduce reaction groups for immobilization on the Au surface, a monolayer of thiol molecules was formed on the Au surface by using the Au-S bond formation reaction, that is, by using the thiolate formation reaction between a linker molecule having a thiol group and Au, to prepare a supporting material. In this reaction, a mixed solution containing two kinds of thiol molecules having an immobilization reaction group and a non-reactive group, respectively, was used. The mole fraction of the thiol molecule having the immobilization reaction group with respect to the total moles of the two thiol molecules was selected to be 5%. In order to introduce a carboxyl immobilization reaction group, 12-mercaptododecanoic acid having a relatively long alkyl chain was used as a linker molecule. As a thiol molecule having a non-reactive group, 6-mercapto-1-hexanol or 1-heptanethiol was used as a matrix molecule. The carboxyl immobilization reaction group was introduced on the surface of the Au wire by placing it in 100 μl of a 2 mM mixed thiol solution in ethanol for 2 hours at room temperature and washing it with absolute ethanol.

The Au wire on which the carboxyl immobilization reaction groups were introduced was placed in 120 μl of an ethanol solution containing 10 mM of 1-ethyl-3-(3-dimetylaminopropyl)carbodiimide (EDC) and 5 mM of N-hydroxysuccinimide (NHS) for 2 hours at room temperature. The carboxyl group was activated by reacting with NHS in the presence of EDC and thus forming NHS-ester.

After activating the carboxyl groups of the thiol monolayer, the Au wire was moved to the enzyme solution containing the active-site masked DNA polymerase. In this step, the activated carboxyl (NHS-ester) of the thiol monolayer reacted with the primary amine of the protein, forming an amide bond (—CO—NH—). As a result, the Taq DNA polymerase was immobilized on the supporting material.

2. Results

As in Example 1, the reaction products were analyzed by electrophoresis. FIG. 7 is a photograph of the electrophoresis results obtained at the reaction times up to 4 hours for every 30 min time interval. As can be seen in FIG. 7, the PCR reaction reaches saturation before 150 minutes.

From the results of Example 1, 2, and 3, the following points can be seen.

Firstly, the nucleic acid sequence amplification apparatus based on the thermal convection according to the present invention works efficiently.

Secondly, it was confirmed that the PCR process can be performed by locating the DNA polymerase immobilized on a solid surface in the low temperature region or in the upper portion of the convection region by using the nucleic acid sequence amplification apparatus based on the thermal convection according to the present invention. It was thus confirmed that DNA polymerases that are not stable at high temperature can also be used.

It should be apparent to those skilled in the art that the present invention described above is not limited to the above embodiments and the attached drawings and that various substitutions, changes, and modifications are possible without departing from the technical ideas of the present invention. Therefore, the above embodiments and modifications are only for illustration, and should not be interpreted to be limiting the present invention. The real scope of the present invention should be determined by the following claims and is not restricted in any way by the specification.

As described above, in the present invention, a plurality of specific regions of the sample are maintained at specific temperatures, and thermal convection among the specific regions makes the sample circulate inside the reaction vessel. Thus, the denaturation, annealing, and polymerization steps can be performed sequentially and repeatedly. Therefore, the following effects can be noted.

Firstly, the nucleic acid sequence amplification apparatus can be designed with a simple composition. The present invention does not require the process for changing the temperature of the sample. Therefore, the design according to the present invention can be made simpler because complex devices included in the prior apparatuses for changing and controlling the sample temperature are not required.

Secondly, the apparatus according to the present invention can be readily miniaturized or integrated into a complex apparatus such as Lab-on-a-chip to perform the PCR nucleic acid sequence amplification process. It can also be incorporated into the apparatuses in which temperature change is not desirable.

Thirdly, DNA polymerases that are not thermostable can also be used. This is because immobilized DNA polymerases can be used in the present invention by locating them in a specific region inside the reaction vessel which region is maintained at a temperature suitable for the polymerase activity. According to the present invention, when an immobilized DNA polymerase is used, PCR can be performed with the immobilized DNA polymerase maintained at the temperature where the polymerase is active. Therefore, according to the present invention, enzymes having their optimal activities at low temperature, such as Klenow fragment or T7 DNA polymerase, may also be used for the PCR process.

Finally, the reaction time for PCR can be reduced. In the present invention, there is no need to change the temperature of the total sample. Thus the time needed for changing and controlling the temperature of the whole sample can be saved.

What is claimed is:

1. A nucleic acid sequence amplification apparatus using PCR, which apparatus comprises:

a plurality of heat sources which supply heat to, or remove heat from a plurality of specific regions in a sample, wherein the plurality of heat sources are arranged to maintain a spatial temperature distribution in the sample such that a first heat source providing heat to a lower portion of the sample is located lower in height than a second heat source removing heat from an upper portion of the sample and a relatively high temperature region is located lower in height than a relatively low temperature region in the sample, wherein the spatial temperature distribution comprises spatial regions fulfilling temperature conditions suitable for (i) a denaturation step in which double strand DNAs become separated to single strand DNAs, (ii) an annealing step in which the single strand DNAs formed in the denaturation step hybridize to the primers to form DNA-primer complexes, or (iii) a polymerization step in which the primers in the DNA-primer complexes are extended by the polymerization reaction, and wherein the apparatus further comprises an insulator positioned between the first and second heat sources.

2. The nucleic acid sequence amplification apparatus of claim 1, wherein at least one of the heat sources comprises a thermally conductive solid in thermal contact with a specific region of the sample; and a heating unit that supplies heat to the thermally conductive solid, or a cooling unit that removes heat from the thermally conductive solid, or a combination of the heating unit and the cooling unit.

3. The nucleic acid sequence amplification apparatus of claim 1, wherein at least one of the heat source comprises a liquid in thermal contact with a specific region of the sample; a receptor in which the liquid is to be contained; and a heating unit that supplies heat to the liquid, or a cooling unit that removes heat from the liquid, or a combination of the heating unit and the cooling unit.

4. The nucleic acid sequence amplification apparatus of claim 3, wherein at least one of the heat sources further comprises a circulation unit that circulates the liquid.

5. The nucleic acid sequence amplification apparatus of claim 1, wherein at least one of the heat sources comprises a gas in thermal contact with a specific region of the sample; a heating unit that supplies heat to the gas, or a cooling unit that removes heat from the gas, or a combination of the heating unit and the cooling unit; and a circulation unit that circulates the gas.

6. The nucleic acid sequence amplification apparatus of claim 1, wherein at least one of the heat sources is an infrared radiation generating unit that supplies heat directly to the sample.

7. The nucleic acid sequence amplification apparatus of claim 1, wherein the plurality of the heat sources comprises a first thermally conductive solid that is in thermal contact with a lower portion of the sample and a second thermally conductive solid that is in thermal contact with an upper portion of the sample.

8. The nucleic acid sequence amplification apparatus of claim 7, wherein the plurality of the heat sources further comprises a third thermally conductive solid that is in thermal contact with an intermediate portion of the sample in between the upper and lower portions.

9. The nucleic acid sequence amplification apparatus of claim 1, wherein the insulator is a solid, liquid or a gas.

10. The nucleic acid sequence amplification apparatus of claim 9, wherein the gas is air.

11. The nucleic acid sequence amplification apparatus of claim 1, wherein the heat sources are further arranged to provide for a spatial temperature distribution comprising a convection region positioned between the relatively high temperature region and the relatively low temperature region.

12. The nucleic acid sequence amplification apparatus of claim 1, wherein at least one of the heat sources comprises a heating unit and a cooling unit.

13. The nucleic acid sequence amplification apparatus of claim 12, wherein the second heat source comprises the heating and cooling units.

14. The nucleic acid sequence amplification apparatus of claim 1 or 12, wherein the apparatus further comprises an opening defined by the plurality of heat sources and the insulator, the opening being adapted to receive a reaction vessel with the sample.

15. The nucleic acid sequence amplification apparatus of claim 14, wherein the opening further comprises a closed bottom end within the first heat source.

16. The nucleic acid sequence amplification apparatus of claim 15, wherein the opening further comprises a first through hole within the second heat source.

17. The nucleic acid sequence amplification apparatus of claim 16, wherein the opening further comprises a second through hole within the insulator.

18. The nucleic acid sequence amplification apparatus of claim 14, wherein the opening is essentially perpendicular to the insulator.

19. The nucleic acid sequence amplification apparatus of claim 14, wherein the opening is configured to receive the reaction vessel configured as a straight cylinder or tube.

20. The nucleic acid sequence amplification apparatus of claim 19, wherein the reaction vessel is further configured to have a single passage between the relatively high temperature region and the relatively low temperature region.

21. The nucleic acid sequence amplification apparatus of claim 20, wherein the single passage is adapted to contain an upward and downward convective flow.

22. The nucleic acid sequence amplification apparatus of claim 19, wherein the reaction vessel is vertical with respect to the heat sources.

23. The nucleic acid sequence amplification apparatus of claim 19, wherein the reaction vessel is pressurized.

24. The nucleic acid sequence amplification apparatus of claim 19, wherein the reaction vessel comprises a top end and a bottom end.

25. The nucleic acid sequence amplification apparatus of claim 24, wherein the bottom end of the reaction vessel is closed.

26. The nucleic acid sequence amplification apparatus of claim 1, wherein the apparatus further comprises multiple reaction vessels.

27. The nucleic acid sequence amplification apparatus of claim 1 or 12, wherein the plurality of heat sources are further arranged to produce a vertical gap between the top of the relatively high temperature region and the bottom of the relatively low temperature region.

28. A nucleic acid sequence amplification apparatus using PCR, which apparatus comprises:
a plurality of heat sources which supply heat to, or remove heat from a plurality of specific regions within an opening configured to receive a reaction vessel and defined by the plurality of heat sources and an insulator,
wherein the plurality of heat sources are arranged to maintain a spatial temperature distribution within the opening such that a first heat source providing heat to a lower portion of the opening is located lower in height than a second heat source removing heat from an upper portion of the opening and a relatively high temperature region is located lower in height than a relatively low temperature region in the opening,
wherein the spatial temperature distribution comprises spatial regions fulfilling temperature conditions suitable for (i) a denaturation step in which double strand DNAs become separated to single strand DNAs, (ii) an annealing step in which the single strand DNAs formed in the denaturation step hybridize to the primers to form DNA-primer complexes, or (iii) a polymerization step in which the primers in the DNA-primer complexes are extended by the polymerization reaction,
the insulator being positioned between the first and second heat sources and in contact with the opening, and further wherein at least one of the heat sources comprises a heating unit and a cooling unit.

29. The nucleic acid sequence amplification apparatus of claim 28, wherein the opening further comprises a closed bottom end within the first heat source.

30. A nucleic acid sequence amplification apparatus using PCR, which apparatus comprises:
a plurality of heat sources which supply heat to, or remove heat from a plurality of specific regions in a sample,
wherein the plurality of heat sources are arranged to maintain a spatial temperature distribution in the sample such that a first heat source providing heat to a lower portion of the sample is located lower in height than a second heat source removing heat from an upper portion of the sample and a relatively high temperature region is located lower in height than a relatively low temperature region in the sample,
wherein the spatial temperature distribution comprises spatial regions fulfilling temperature conditions suitable for (i) a denaturation step in which double strand DNAs become separated to single strand DNAs, (ii) an annealing step in which the single strand DNAs formed in the denaturation step hybridize to the primers to form DNA-primer complexes, or (iii) a polymerization step in which the primers in the DNA-primer complexes are extended by the polymerization reaction,
and further wherein at least one of the heat sources comprises a heating unit and a cooling unit.

31. The nucleic acid sequence amplification apparatus of claim 28 or 30, wherein at least one of the heat source comprises a liquid in thermal contact with a specific region of the sample; and a receptor in which the liquid is to be contained.

32. The nucleic acid sequence amplification apparatus of claim 31, wherein at least one of the heat sources further comprises a circulation unit that circulates the liquid.

33. The nucleic acid sequence amplification apparatus of claim 28 or 30, wherein at least one of the heat sources comprises a gas in thermal contact with a specific region of the sample; a heating unit that supplies heat to the gas, or a cooling unit that removes heat from the gas, or a combination of the heating unit and the cooling unit; and a circulation unit that circulates the gas.

34. The nucleic acid sequence amplification apparatus of claim 28 or 30, wherein at least one of the heat sources is an infrared radiation generating unit that supplies heat directly to the sample.

35. The nucleic acid sequence amplification apparatus of claim 28 or 30, wherein the plurality of the heat sources comprises a first thermally conductive solid that is in thermal contact with a lower portion of the sample and a second thermally conductive solid that is in thermal contact with an upper portion of the sample.

36. The nucleic acid sequence amplification apparatus of claim 35, wherein the plurality of the heat sources further comprises a third thermally conductive solid that is in thermal contact with an intermediate portion of the sample in between the upper and lower portions.

37. The nucleic acid sequence amplification apparatus of claim 28, wherein the insulator is a solid, liquid or a gas.

38. The nucleic acid sequence amplification apparatus of claim 37, wherein the gas is air.

39. The nucleic acid sequence amplification apparatus of claim 28 or 30, wherein the heat sources are further arranged to provide for a spatial temperature distribution comprising a convection region positioned between the relatively high temperature region and the relatively low temperature region.

40. The nucleic acid sequence amplification apparatus of claim 28 or 30, wherein the second heat source comprises the heating and cooling units.

41. The nucleic acid sequence amplification apparatus of claim 30, wherein the apparatus further comprises an opening defined by the plurality of heat sources and an insulator, the opening being adapted to receive a reaction vessel with the sample.

42. The nucleic acid sequence amplification apparatus of claim 41, wherein the opening further comprises a closed bottom end within the first heat source.

43. The nucleic acid sequence amplification apparatus of claim 42, wherein the opening further comprises a first through hole within the second heat source.

44. The nucleic acid sequence amplification apparatus of claim 43, wherein the opening further comprises a second through hole within the insulator.

45. The nucleic acid sequence amplification apparatus of claim 41, wherein the opening is essentially perpendicular to the insulator.

46. The nucleic acid sequence amplification apparatus of claim 41, wherein the opening is configured to receive the reaction vessel configured as a straight cylinder or tube.

47. The nucleic acid sequence amplification apparatus of claim 46, wherein the reaction vessel is further configured to have a single passage between the relatively high temperature region and the relatively low temperature region.

48. The nucleic acid sequence amplification apparatus of claim 47, wherein the single passage is adapted to contain an upward and downward convective flow.

49. The nucleic acid sequence amplification apparatus of claim 46, wherein the reaction vessel is vertical with respect to the heat sources.

50. The nucleic acid sequence amplification apparatus of claim 46, wherein the reaction vessel is pressurized.

51. The nucleic acid sequence amplification apparatus of claim 46, wherein the reaction vessel comprises a top end and a bottom end.

52. The nucleic acid sequence amplification apparatus of claim 51, wherein the bottom end of the reaction vessel is closed.

53. The nucleic acid sequence amplification apparatus of claim 28 or 30, wherein the apparatus further comprises multiple reaction vessels.

54. The nucleic acid sequence amplification apparatus of claim 28 or 30, wherein the plurality of heat sources are further arranged to produce a vertical gap between the top of the relatively high temperature region and the bottom of the relatively low temperature region.

55. The nucleic acid sequence amplification apparatus of claim 28 or 30, wherein at least one of the heat sources comprises a thermally conductive solid in thermal contact with a specific region of the sample; the heating unit supplying heat to the thermally conductive solid, and the cooling unit removing heat from the thermally conductive solid.

* * * * *

```
                              SEQUENCE LISTING

<160> NUMBER OF SEQ ID NOS: 7

<210> SEQ ID NO 1
<211> LENGTH: 17
<212> TYPE: DNA
<213> ORGANISM: Artificial
<220> FEATURE:
<223> OTHER INFORMATION: Synthetic sequence

<400> SEQUENCE: 1
attaaccctc actaaag                                                        17

<210> SEQ ID NO 2
<211> LENGTH: 17
<212> TYPE: DNA
<213> ORGANISM: Artificial
<220> FEATURE:
<223> OTHER INFORMATION: Synthetic sequence

<400> SEQUENCE: 2
aatacgactc actatag                                                        17

<210> SEQ ID NO 3
<211> LENGTH: 17
<212> TYPE: DNA
<213> ORGANISM: Artificial
<220> FEATURE:
<223> OTHER INFORMATION: Synthetic sequence

<400> SEQUENCE: 3
cgaggtcgac ggtatcg                                                        17

<210> SEQ ID NO 4
<211> LENGTH: 17
<212> TYPE: DNA
<213> ORGANISM: Artificial
<220> FEATURE:
<223> OTHER INFORMATION: Synthetic sequence

<400> SEQUENCE: 4
gtaaaacgac ggccagt                                                        17

<210> SEQ ID NO 5
<211> LENGTH: 17
<212> TYPE: DNA
<213> ORGANISM: Artificial
<220> FEATURE:
<223> OTHER INFORMATION: Synthetic sequence

<400> SEQUENCE: 5
tggcgaaagg gggatgt                                                        17

<210> SEQ ID NO 6
<211> LENGTH: 17
<212> TYPE: DNA
<213> ORGANISM: Artificial
<220> FEATURE:
<223> OTHER INFORMATION: Synthetic sequence

<400> SEQUENCE: 6
ggcgaacgtg gcgagaa                                                        17
```

```
<210> SEQ ID NO 7
<211> LENGTH: 65
<212> TYPE: DNA
<213> ORGANISM: Artificial
<220> FEATURE:
<223> OTHER INFORMATION: Synthetic sequence

<400> SEQUENCE: 7
tctagaacta gtggatcctt ttcttttctt gaattctttc ttttcttttaa tcgataccgt    60 cgacc                                                                65
```